United States Patent [19]

Gale et al.

[11] Patent Number: 4,698,062

[45] Date of Patent: Oct. 6, 1987

[54] MEDICAL DEVICE FOR PULSATILE TRANSDERMAL DELIVERY OF BIOLOGICALLY ACTIVE AGENTS

[75] Inventors: Robert M. Gale, Los Altos; Randall Berggren, Livermore, both of Calif.

[73] Assignee: ALZA Corporation, Palo Alto, Calif.

[21] Appl. No.: 792,941

[22] Filed: Oct. 30, 1985

[51] Int. Cl.$^4$ ................................................ A61K 9/00
[52] U.S. Cl. ..................................... 604/896; 424/449
[58] Field of Search .............................. 604/890–893, 604/896, 897; 424/19–22, 28

[56] References Cited

U.S. PATENT DOCUMENTS

| | | | |
|---|---|---|---|
| 3,625,214 | 12/1971 | Higuchi | 424/21 |
| 3,797,494 | 3/1974 | Zaffaroni | 604/897 |
| 4,031,894 | 6/1977 | Urquhart et al. | 604/897 |
| 4,291,015 | 9/1981 | Keith et al. | 604/896 |
| 4,336,243 | 6/1982 | Sanvordeker et al. | 604/897 |
| 4,379,454 | 4/1983 | Campbell et al. | 604/897 |
| 4,486,193 | 12/1984 | Shaw et al. | 604/897 |
| 4,559,054 | 12/1985 | Bruck | 604/892 |

Primary Examiner—C. Fred Rosenbaum
Assistant Examiner—Jerome R. Smith, Jr.
Attorney, Agent, or Firm—Steven F. Stone; Edward L. Mandell; Paul L. Sabatine

[57] ABSTRACT

A medical device and method for the pulsatile administration of a drug through intact skin at a first steady state flux during a first delivery period and a second steady state flux during a second delivery period, said first flux being substantially higher than said second flux; said first and second delivery periods comprising a substantial portion of a predetermined administration period. The device comprises a reservoir of said drug containing an amount of drug sufficient to administer drug at said first and second steady state fluxes during administration period; a reservoir of a skin permeation enhancer for said drug; said reservoir containing an amount of said permeation enhancer sufficient to permit administration of said drug at said first flux only through said first delivery period; and means for maintaining said device on the skin in drug and permeation enhancer transferring relationship thereto a preferred embodiment delivering nitroglycerin and employing ethanol as a permeation enhancer. The device contains means for controlling the maximum delivery rate of one of said drug or enhancer. A preferred embodiment provides for the pulsatile delivery of nitroglycerin.

35 Claims, 8 Drawing Figures

MEDICAL DEVICE FOR PULSATILE TRANSDERMAL DELIVERY OF BIOLOGICALLY ACTIVE AGENTS

FIELD OF THE INVENTION

This invention relates to medical devices for delivering biologically active agents (hereinafter referred to generally as "drugs") to the body through intact skin and more particularly for the pulsatile delivery of drugs at at least two different predetermined rates during predetermined portions of a predetermined administration period.

BACKGROUND OF THE INVENTION

Medical devices that deliver drugs through the skin for absorption into the body have been known for some time. For example, U.S. Pat. No. 3,249,109 describes a two-layer topical dressing that consists of an adhesive base made of drug-containing hydrated gelatin with a fabric backing layer. This type of device delivers a varying amount of drug to the skin and the rate of absorption is determined by the release rate of drug from the device which decreases as a function of time of application and permeability of the skin at the administration site. In order to transdermally deliver drugs having a relatively narrow therapeutic range, and for which such wide variations could not be tolerated, "system-controlled" delivery devices, which deliver drugs transdermally at rates which are controlled primarily by the delivery device, were developed to reduce or eliminate the variations in delivery rate associated the uncontrolled devices described above. For example, U.S. Pat. No. 3,598,122 describes a multilayer adhesive bandage for delivering drugs into the systemic circulation formed of a backing layer, a drug reservoir layer, a contact adhesive layer, and includes means for metering the rate at which the drug is released to the skin. Other representative system controlled transdermal drug delivery devices are described in U.S. Pat. Nos. 3,797,494 and 4,379,454, the latter of which teaches controlling the rate at which a drug is absorbed through the skin by controlling the rate at which a permeation enhancer for the drug is delivered to the skin. (All of the aforementioned U.S. patents are incorporated herein by reference.) In addition, Black, "Transdermal Drug Delivery systems", U.S. Pharmacist, November, 1982, pp. 49-78, provides additional background information regarding commercially available transdermal drug delivery systems and a reasonably representative summary of the factors involved in percutaneous absorption of drugs may be found in Aritz, et al., "Studies on Percutaneous Absorption of Drugs", *Chem. Phar. Bull.*, Vol. 18, 1970, pp. 1045-1049; Idson, "Percutaneous Absorption", *J. Phar. Sci.*, Vol. 64, No. 6, pp. 910-922; and Cooney, *Advances in Biomedical Engineering*, Part 1, Chapter 6, "Drug Permeation Through Skin: Controlled Delivery for Topical Systemic Therapy", Marcel Dekker, Inc., New York and Basel 1980, pp. 305-318.

Although the transdermal drug delivery route is rapidly becoming a preferred delivery route for a wide variety of drugs, transdermal delivery is not without its problems. For example, transdermal systems generally have a relatively long lag time between the time the device is applied to the skin and the time that therapeutic levels are achieved in the blood. This is because the transfer of the therapeutic agent from the device into the bloodstream is a diffusional process and requires the necessary concentration gradient to be established between the device and the internal surfaces of the skin. Attempts to decrease the lag time have been proposed and include a "pulse" dosage of the drug in the adhesive layer in contact with the skin in order to initially saturate the skin binding sites so that delivery into the systemic circulation can begin sooner and treatment of the skin with permeation enhancers, either prior to administration of the device or concurrently with the drug administration. (See for example, U.S. Pat. No. 4,031,894 which is incorporated herein by reference.)

A more fundamental limitation of the rate controlled and non-rate controlled devices of the prior art is that they are designed to deliver a drug into the systemic circulation at either a substantially constant rate throughout a substantial portion of the administration period or at a generally declining rate with time of administration. In many circumstances it would be extremely desirable to achieve and maintain an initially high blood level of a drug for a significant portion of the administration period and therafter maintain a lower, but still constant, blood level for the remainder of the administration period. This type of dosage regime would be desirable in those instances in which a rapid onset of therapeutic effect is desired. Rapid onset could be obtained from a high initial blood level which could not be tolerated for the entire administration period due to the undesirable side effects that could result from the maintenance of the high blood level. Thus drug blood levels for the remainder of the administration period would have to be reduced to a lower, but still constant, therapeutic level. Such a dosage regime would also be desirable in administration of a drug which may create a tolerance to the therapeutic effect if the drug is administered at a constant continuous rate. In such circumstances for example, the initial high blood levels may be more effective when followed by a lower maintenance level than if the blood levels were maintained either at the higher or the lower level throughout the entire administration period. Nitroglycerin, for example, could be delivered in such a regime.

It is therefore a primary object of this invention to provide a transdermal drug delivery device adapted to administer a drug throughout a predetermined administration period in which the drug is delivered at a first, higher, substantially constant rate for a significant portion of the delivery period followed by a second, and lower, substantially constant delivery rate for the remainder of the administration period. Such a device is particularly suitable for delivering drugs which are capable of permeating through normal skin at rates which produce therapeutic doses from reasonably sized devices without the use of permeation enhancers. It also contemplated that the device could be employed to deliver drugs which are less permeable if the skin at the delivery site is pretreated to increase its permeability by perforating, stripping, abrading or chemically treating the stratum corneum.

It is another object of this invention to provide a pulsatile transdermal drug delivery device.

It is another object of the device to provide a transdermal drug delivery device capable of delivering a drug into the systemic circulation substantially constant delivery rates within sequential predetermined portions of predetermined administration period.

It is another object of this invention to provide a method for the pulsatile transdermal delivery of a drug.

These and other objects of this invention will be readily apparent from the following description with reference to the accompanying drawings, wherein.

DESCRIPTION OF THE INVENTION

Figure 1:
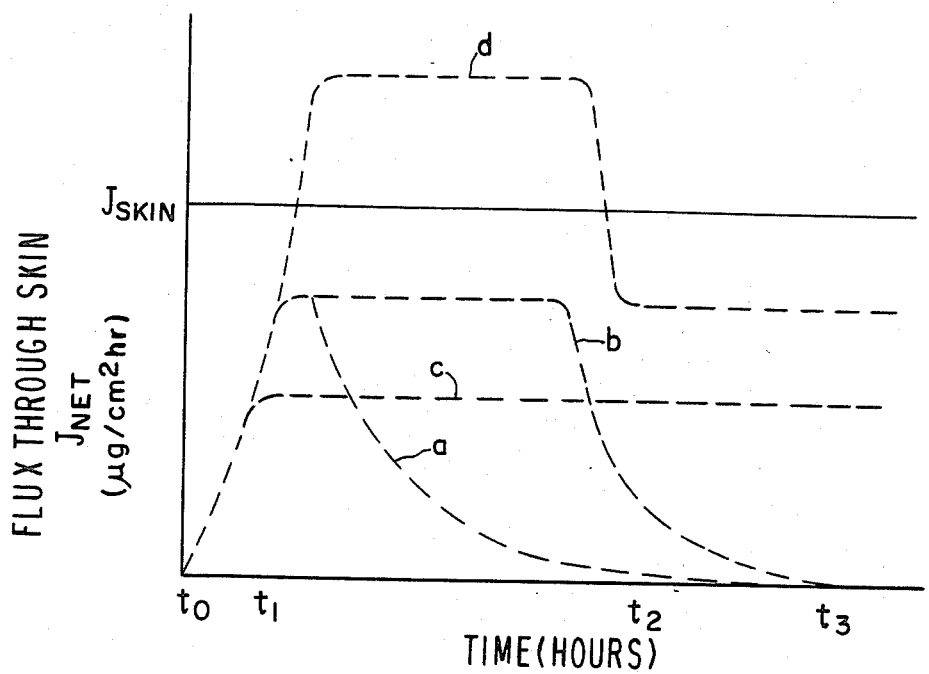
FIG. 1 is a plot of theoretical in vitro release rates through cadaver skin into an infinite sink of typical transdermal delivery devices of the prior art and of this invention.

To facilitate an understanding of this invention and the distinctions between the claimed subject matter and the prior art, a brief description of the in vitro release rate profiles of existing transdermal drug delivery devices is helpful. FIG. 1 compares the idealized release pattern obtained from various devices of the prior art to that obtained according to our invention. It will be noted that with respect to most systems there is an initial, transient, release period running form $t_0$ to $t_1$ in which there is a rapid increase of the rate of release into an infinite sink through human cadaver skin from the device which results from the initial loading of the drug at the surface in contact with the skin. After this initial transient period has expired, the uncontrolled devices such as disclosed in U.S. Pat. No. 3,249,109 will exhibit, depending on the initial drug loading, either a generally decreasing, steady-state release rate with time from $t_1$-$t_3$ which is typically a function of $t^{-\frac{1}{2}}$ (Curve a), or a pattern (Curve b) characterized by a substantially constant steady-state rate period from $t_1$-$t_2$ in which the concentration of the agent is sufficient to permit the delivery rate to be limited by the skin until the concentration of the drug in the device drops at $t_2$ to the level at which a second, decreasing steady-state rate is established which decays as a function of $t^{-\frac{1}{2}}$ similar to that of Curve a. The time between $t_1$ and $t_2$ is determined by the initial drug loading and the permeability of the system itself.

When a rate controlled device is used a pattern such as shown in Curve c is obtained. A rate controlled device is typically designed to release agent at a rate lower than that obtainable through skin of average permeability and to contain sufficient drug such that unit activity (saturation concentration) is maintained throughout the steady-state portion of the delivery period running from $t_1$-$t_3$. If less drug were contained within the device so that unit activity ceased at $t_2$, the period between $t_2$ and $t_3$ would exhibit a pattern substantially similar to that of Curve b.

According to out invention a release rate pattern such as shown by Curve d is intended to be achieved. Such a pattern would be extremely useful in connection wih drugs such as analgesics, anti-emetics, anti-inflammatories, anti-anginals, and anti-spasmodics in which it is desirable to bring about a rapid onset of the treatment or where an initial higher blood level is required to treat acute symptoms and a continued lower dose rate is desired to prevent recurrence or to sustain therapy after the initial acute phase has been resolved. Also, with respect to drugs which may induce tolerance, the initial higher blood level may be required to overcome the pre-existing tolerance and a lower blood level is required to be maintained to prevent recurrence of symptoms or to prevent the development of other undesirable side effects which may occur if drug administration is terminated completely.

According to our invention the total administration time $t_0$-$t_3$ would normally be at least 16 hours and usually 24 hours to 7 days. The maximum practical time period of transdermal delivery is usually limited by the time during which a system can be maintained in contact with the skin without producing undesirable effects from occlusion or irritation. When adhesive systems are utilized it is normally not practical to transdermally deliver a drug beyond the 7 day period in which the human skin surface layer is replaced from the underlying tissue.

The steady-state portion of the administration period is that portion of the administration period beginning at the end of the initial transient period ($t_0$-$t_1$) and running to the end of the predetermined administration period, as represented by $t_1$-$t_3$ even though the delivery rate itself may not, as noted above, be constant throughout the steady-state period.

According to this invention a steady-state delivery rate is considered to be substantially constant if it does not vary more than about $\pm 20\%$ during the involved time period. The time periods during which the higher and lower steady-state delivery rates are to be maintained will, of course, be dependent on the drug being delivered. Typically the time periods would each be at least about 2-3 hours and preferably at least about 5 hours.

It should be noted, however, that the blood level achieved from a release rate pattern does not necessarily parallel the release rate curve. This is because of factors such as skin binding, and also because of the competing rates of drug delivery into the blood and drug clearance from the blood as a result of metabolic action on the drug in the skin or body.

Figure 2:
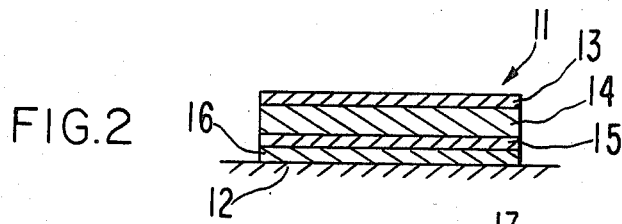
FIGS. 2-5 are cross-sectional views through embodiments of transdermal delivery devices according to this invention.

FIGS. 2-5 disclose embodiments of medical devices according to this invention which in their general construction are similar to those disclosed in the aforementioned U.S. Pat. No. 4,379,454 although differing in certain critical characteristics as will be more specifically described below. Thus, for example, FIG. 2 illustrates a self-adhering skin patch 11 designed to be placed on unbroken skin 12. Device 11 is a laminate that consists of four layers, an impermeable top backing layer 13, a drub/permeation enhancer reservoir layer 14, a rate controlling membrane layer 15, and a contact adhesive layer 16. Backing layer 13 is made from a material or combination of materials that is substantially impermeable to the components of lamina 14. It serves as a protective cover for the patch, keeps the components of reservoir layer 14 from escaping from the bandage, and fulfills a structural support function. In embodiments of the invention in which reservoir layer 14 is fluid, the outer edge of the backing layer will overlay the edge of the reservoir layer and be sealed by adhesion or fusion to the rate controlling membrane. In such structures the reservoir layer is contained wholly between the backing layer and the membrane layer and does not have any exposed surfaces. The backing and rate controlling membrane may be inherently sealable to each other or may include sealing means, such as an additional layer or adhesive, in such embodiments.

Reservoir layer 14 is immediately below backing 13. It contains supplies of both the permeation enhancer and the drug. Rate controlling membrane layer 15, the next layer of the device may be made of a dense or microporous polymer film that has the requisite permeability to the drug and permeation enhancer. It is the element of path 11 that controls the rate at which the permeation enhancer and drug are delivered to the skin. The respective fluxes of the drug and enhancer through layer 15 will depend upon the thickness of the layer, its diffusion coefficients relative to the drug and the enhancer, and the concentration and loading of permeation enhancer in the reservoir. The diffusion coefficients of the layer 15 for a particular drug and enhancer may be determined by standard techniques. Examples of the types of polymer films that may be used to make layer 15 are disclosed in U.S. Pat. Nos. 3,797,494 and 4,021,894 which are incorporated herein by reference.

Contact adhesive lamina 16 is directly below diffusion membrane layer 15. It is one means for which device 11 may be affixed to the area of skin to be treated. Its composition and thickness are normally such that it does not constitute a significant permeation barrier to either the drug or the enhancer, and normally it will be substantially more permeable to the drug enhancer than layer 15. During the time interval between the manufacture and the use of device 11, layer 16 may absorb enhancer and drug in amounts that will depend upon the composition, solubility of the components in layer 16, and the length of the time interval. If the interval is quite long, layer 16 will absorb enhancer and the drug until it is saturated with both. Contact adhesive compositions that may be used to make layer 16 are disclosed in the aforementioned U.S. Pat. Nos. 3,797,494 and 4,031,894.

Prior to use, device 11 also includes a protective undercoating layer made from materials that are substantially impermeable to the drug, the enhancer, and any other components of layer 16. The same materials that are used to make backing layer 13 maybe used to make the undercoating layer, provided they are made strippable such as by siliconizing (not shown). Just prior to use, the undercoating is pulled away from adhesive 16 and discarded. Device 11 is then applied to a relatively nonhairy area of skin 12 that is substantially free of wrinkles, creases, or folds. Various locations on the torso, such as the flank, chest, or shoulder, provide suitable sites for the bandage. As indicated above, once it is placed on the skin the bandage will begin co-administering drug and permeation enhancer to the wearer.

Figure 6:
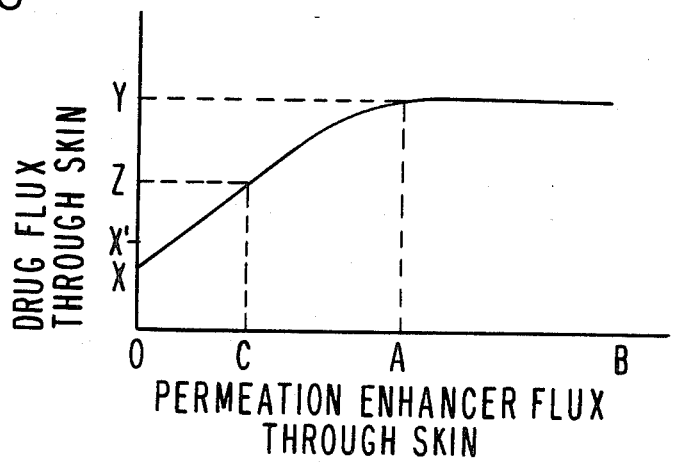
FIG. 6 is a plot of in vitro drug flux through skin as a function of permeation enhancer flux through skin.
Figure 7:
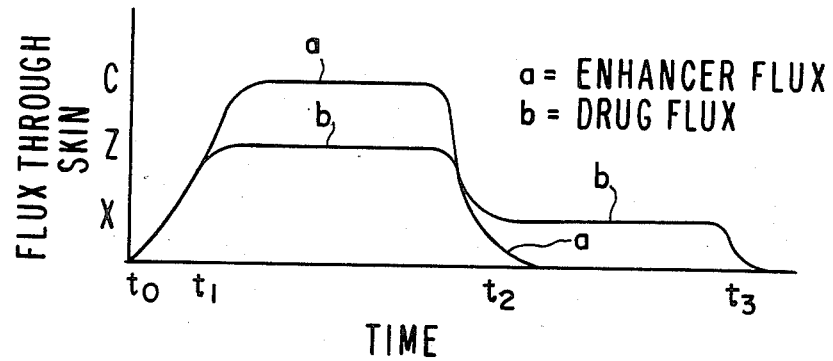
FIG. 7 is a plot of in vitro nitroglycerin and ethanol fluxes through cadaver skin into an infinite sink as a function of time according to this invention.

In order to obtain the pulsatile drug delivery pattern desired according to this invention, instead of the substantially constant delivery pattern obtained according to the aforementioned U.S. Pat. No. 9,379,454 it is important that medical devices according to this invention possess certain critical characteristics. Referring now to FIGS. 6 and 7 typical plots for the relationship between drug flux through skin and permeation enhancer flux through skin are shown. It can be seen from FIG. 6 that at permeation enhancer fluxes in the range of 0 to A there is a more or less direct relationship between enhancer flux and drug flux, with the drug flux increasing from the level X, at which the drug permeates through untreated skin, to level Y. At enhancer fluxes greater than A and up to level B, at which irreversible changes are created in the skin, there may, in many cases, be no significant increase in drug delivery rate with enhancer flux.

A representative pulsatile drug delivery device according to this invention therefore would be designed to deliver, during the high, steady state delivery rate regime, drug at a rate greater than X, and at any level up to Y, which for example is shown at Z in FIGS. 6 and 7. In order to achieve drug flux Z, rate controlled membrane 15 may either control the delivery rate of the drug or the permeation enhancer. Thus for example, if membrane 15 were to control the enhancer delivery rate its characteristics would be selected such that the enhancer flux through skin would be at level C as shown in FIGS. 6 and 7. If, on the other hand, membrane 15 were selected to control the drug flux; the enhancer would be delivered in substantial excess such that the enhancer flux through skin during the initial steady state period is in excess of C but less than B. The membrane 15, in that case, would be selected to reduce the drug flux through skin down to level Z. At the commencement of the second and lower steady state delivery rate regime the enhancer flux drops rapidly below level C, causing the the drug flux through skin to drop to level X, the rate at which the drug permeates through substantially untreated skin or the level X' a slightly higher level equivalent to the rate at which drug permeates through skin which has been previously treated with a permeation enhancer but in the absence of continuous permeation enhancer delivery. Level X' may be slightly higher than X due to some small, transient and non-damaging changes in the properties of the skin.

In order to accomplish the desired pulsatile delivery according to this invention the loadings of the drug and the permeation enhancer are critical. The loading of the drug must be at least equal to the total dose at the selected delivery rates for at least the predetermined administration period, $t_0$–$t_3$, and sufficient to maintain the drug at or above unit activity throughout substantially all of the time period $t_0$–$t_3$. The loading of permeation enhancer, however, can be no greater than that required to deliver enhancer within the selected flux range only until the expiration of the high steady state delivery rate regime at $t_2$. At the termination of the high rate regime, the activity of the permeation enhancer in the reservoir should be depleted so that the enhancer flux rapidly drops below level C.

This invention is applicable to a wide variety of drugs and permeation enhancers, within certain constraints imposed by the nature of the invention. For example, a drug to be usable according to this invention without pretreatment of the skin would have to have sufficient permeability through normal skin to produce a therapeutic effect when administered at flux level X or X'. Similarly, the permeation enhancer would have to be of the type that does not produce substantial changes in the properties of the skin that are rapidly reversible when the permeation enhancer is removed. Suitable permeation enhancers will vary from drug to drug but include ethanol, n-decylmethyl sulfoxide (nDMS), dimethyl lauramide, and polyethylene glycol monolaurate (PEGML), for example. Unsuitable permeation enhancers are of the type that appear to produce non-transient changes in the skin which include dimethylsulfoxide, for example.

Figure 3:
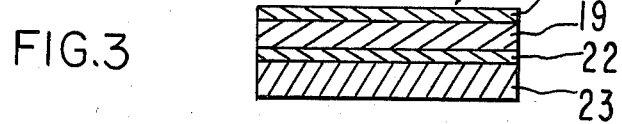

Referring now to FIG. 3, another embodiment of the invention, generally designated 17, is shown in which the drug and enhancer are stored in separate reservoirs.

Device 17 is composed of four layers, a backing layer 18, a permeation enhancer reservoir layer 19, a rate controlling membrane layer 22 and a drug reservoir-contact adhesive layer 23. Layer 18 is identical in structure and function to layer 13 of embodiment 11. Layer 19 contains the supply of percutaneous absorption enhancer. As in FIG. 1 the loading of enhancer in layer 19 will depend on the rate and duration of enhancer administration required to achieve the desired pulsatile drug delivery. Layer 22 is the component of device 17 that controls the release rate of enhancer to the skin. In this regard it is structurally, compositionally and functionally similar to membrane 15 of embodiment 11. Because the drug does not pass through layer 22, layer 22 need not be permeable to the drug. Indeed it is preferred that it be substantially impermeable to the drug to minimize upward migration of the drug from the drug reservoir layer 23. Layer 23 contains the supply of drug admixed with a contact adhesive composition, with the loading of drug depending on the rates at which the drug is delivered and the duration of the total therapeutic administration period. Layer 23 may be a uniform dispersion of drug in adhesive or layer 23 may be separated into a distinct drug reservoir layer composed of the drug supply within a suitable matrix material and a distinct contact adhesive layer underlying the drug reservoir layer. In any case, the drug loading is preferably sufficient to maintain the the concentration of the drug in layer 23 at or above saturation from $t_0$-$t_3$. This permits a unit activity source to be available for delivery throughout the entire administration period and assists in maintenance of a constant delivery rate in both phases of the pulsatile delivery. As with the device of FIG. 2, it is also possible to control the release rate of drug and deliver the enhancer in an uncontrolled manner. In that instance, layer 19 would be the drug reservoir, layer 22 would maintain drug flux at level Y and layer 23 would contain the enhancer at a loading such that the enhancer flux would drop rapidly below level C after $t_2$.

Embodiments such as device 17 in which the drug and enhancer supplies are separate may be advantageous or necessary in instances where formulation or storage of the drug and enhancer in contact with each other is impractical or undesirable or where separation of the drug and enhancer make selection of the rate controlling membrane easier.

Figure 4:
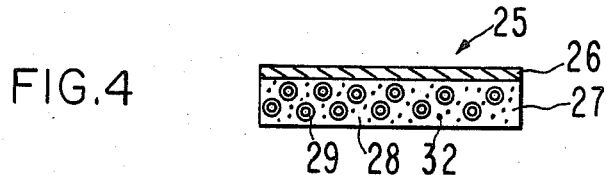

FIG. 4 illustrates another embodiment, generally designated 25, in which the supplies of drug and enhancer are separate. Device 25 is a laminate composed of two layers, a backing layer 26 and a heterogenous, microcapsule-containing basal layer 27. Backing layer 26 is structurally, compositionally, and functionally identical to layer 13 of embodiment 11. heterogeneous basal layer 27 is composed of a continuous matrix phase 28 in which enhancer-containing microcapsules 29 and drug 32 (represented by stippling in FIG. 4) are dispersed. Continuous matrix phase 28 is a solid, semisolid or gel composition that is permeable to the enhancer and the drug. It preferably adheres to skin. If it does not, an adhesive overlay will have to be used to keep embodiment 25 in contact with the skin. The contact adhesive compositions that are used to make the contact adhesive layers of embodiment 11 and 17 will usually be suitable for use as continuous matrix phase 28. Microcapsules 29 each consist of an inner core of permeation enhancer encapsulated by a rate controlling membrane. The membrane functions as membranes 15 and 22 and may be made of the same materials and be selected based on the same criteria as membranes 15 and 22. Accordingly, the membrane on each microcapsule controls the rate at which the enhancer is released therefrom. The combined release of enhancer from all the microcapsules in turn defines the rate of release of enhancer from embodiment 25. As in the case of the other embodiments the loading of enhancer contained in layer 27 in microcapsule form will depend upon the required enhancer release rate and duration of the high delivery rate phase. Microcapsules 29 may be made using conventional microcapsule forming techniques. Drug 32 is preferably present dissolved and dispersed in continuous phase 28, the loading of drug present in layer 27 being at least that required to provide a unit activity drug source throughout the period of therapy. The particular amount present in a given instance will depend upon the rate at which the drug is absorbed by the skin from layer 27 and the duration of therapy. The thickness and composition of continuous phase 28 should be such that it does not constitute a principal permeation barrier to either the enhancer or the drug. As with respect to the devices. FIGS. 2 and 3 the drug could be encapsulated in the microcapsules and the permeation enhancer dispersed in layer 27 with the same constraints as described with respect to FIGS. 2 and 3.

Figure 5:
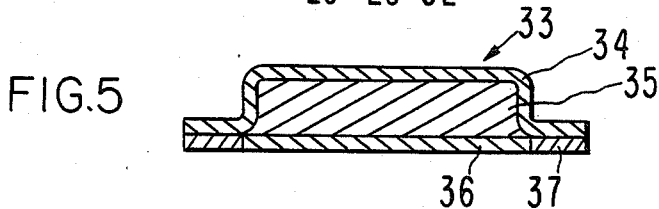

FIG. 5 shows another embodiment of the invention, generally designated 33. The components of device 33 are backing layer 34, a reservoir layer 35 that contains supplies of permeation enhancer and drug, a diffusion membrane layer 36, and a peripheral ring 37 of contact adhesive. Device 33 is structurally, functionally, and compositionally identical to device 11 except in the following respects. First, the contact adhesive component of device 33 is in the form of a peripheral ring rather than a continuous basal layer. Neither drug nor enhancer passes through ring 37 and it, therefore, need not be permeable to these compositions. Secondly, the basal surface from which drug and enhancer is transferred to the skin is defined by rate controlling membrane layer 36. Thirdly, the backing layer is not flat but instead forms a pocket or cavity in which the reservoir layer is held. Lastly, the outer edge of the backing layer is sealed to the peripheral ring of contact adhesive.

The embodiments of FIGS. 2–5 may be designed to administer drug and enhancer at the rates required to achieve the desired pulsatile drug therapy. In order to determine the optimum rates for a given drug-enhancer combination it is necessary to determine the permeability of skin to the drug and the permeation enhancer and the relationship between the drug flux and enhancer flux through skin.

The following discussion will illustrate the techniques employed in designing pulsatile transdermal delivery devices according to this invention with respect to a transdermal drug delivery device for delivering nitroglycerin in a pulsatile mode. A high rate of approximately 80 $\mu g/cm^2/hr$ for the initial steady state period of approximately 6 hours and at a rate of approximately 35 $\mu g/cm^2/hr$ for the remainder of a 24 hour administration period were selected as targets and normal having the average permeabilities to nitroglycerin and ethanol of normal human skin were used as design criteria.

The steady state, in vivo drug input rate, Jnet, of an agent, such as a drug or permeation enhancer delivered through the skin from a transdermal delivery device is given by the following relationship:

$$1/J_{net} = 1/J_{skin} + 1/J_{device} \qquad (1)$$

wherein $J_{device}$ is in the in vitro steady state flux of agent from the device directly into an infinite sink an $J_{skin}$ is the in vivo or in vitro steady state inherent flux of agent directly through skin from a unit activity source into an infinite sink, all units being expressed in $\mu g/cm^2 hr$.

Figure 8:
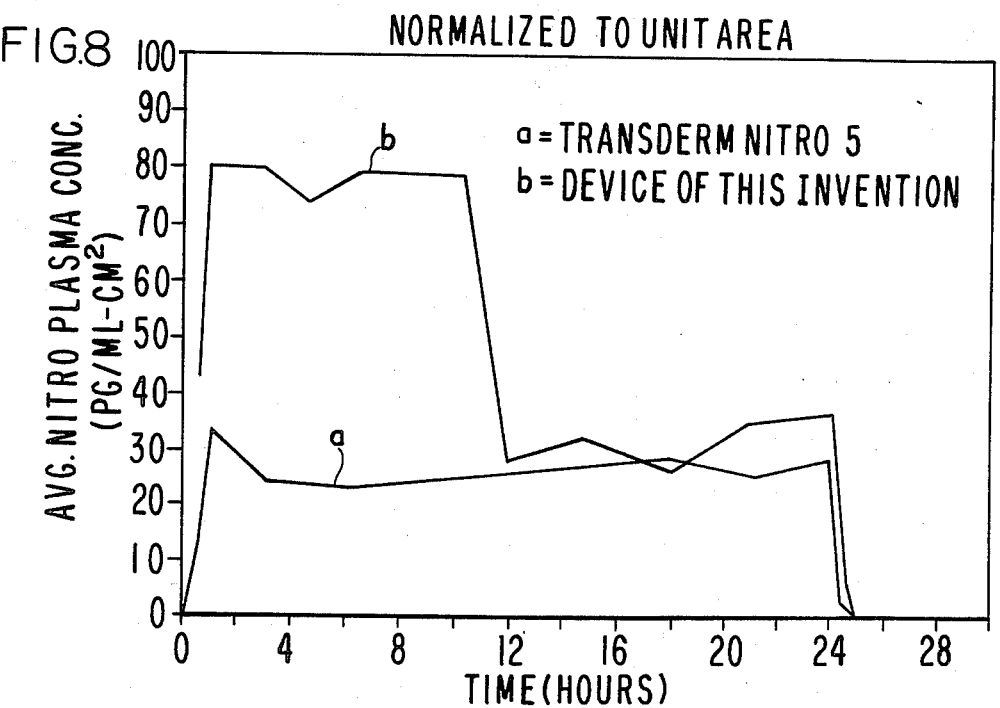
FIG. 8 is a plot of nitroglycerin plasma levels as a function of time for an embodiment of this invention.

The permeability of normal human skin to NG, is in the range of about 10–50 $\mu g/cm^2$ the average being about 40 $\mu g/cm^2 hr$. For this embodiment, the lower NG delivery flux of 35 $\mu g/cm^2 hr$ will be used to establish the $J_{device}$ (NG) in the absence of a permeation enhancer and the upper NG delivery rate of 80 $\mu g/cm^2 hr$ will determine the additional characteristics required for the initial phase. In order to permit the skin to primarily control the lower steady state rate, the $J_{device}$ (NG) must be substantially higher than $J_{skin}$ (NG). For example, application of Formula 1 shows that $J_{device}$ (NG) should be at least about 280 $\mu g/cm^2hr$.

To achieve the initial high in vivo drug fluxes contemplated herein, a permeation enhancer must be delivered in the initial phase at a flux sufficient to increase the $J_{net}$ (NG) to about 80 $\mu g/cm^2hr$. ethanol, within certain flux ranges produces a non-damaging, reversible effect on skin permeability, and is suitable for use as a NG permeation enhancer according to this invention. The delivery device of this example therefore should be designed to deliver ethanol at a flux sufficient to increase the NG permeability of the skin to a value no less than the $J_{net}$ of NG in the high initial phase and preferably substantially higher.

It has been determined that ethanol can reversibly increase the $J_{skin}$ (NG) for average skin to levels greater than 80 $\mu g/cm^2hr$ if the $J_{net}$ of ethanol delivered through the skin is at least about 250 $\mu g/cm^2hr$ and preferably higher but no greater than about 500 $\mu g/cm^2hr$, the level at which unacceptable and temporarily irreversible skin changes are observed. The permeability of average human skin to ethanol is in the range of about 1200 to 1500 $\mu g/cm^2hr$. Therefore the ethanol $J_{device}$ according to this invention is preferably in the range of about 300 to 750 $\mu g/cm^2hr$ to obtain the average target ethanol $J_{net}$ of about 250–500 $\mu g/cm^2hr$. Ethylene vinyl acetate (EVA) membranes having a vinyl acetate (VA) content of at least 11% and preferably in the range of 12–18% possess the necessary characteristics to maintain the fluxes of both NG and ethanol within the respective ranges required according to this invention.

It is also necessary that certain drug and ethanol loadings be initially present in the reservoir such that the delivery device will function to delivery NG at the selected rates throughout the selected portions of the 24 hour administration period, and ethanol at the desired rate only for the initial high delivery rate phase of about 10 hours.

The minimum initial NG loading per $cm^2$ of the system is determined by the solubility of the NG in the matrix and the in vivo delivery rates, sufficient NG being initially present to maintain a unit thermodynamic activity of NG in the reservoir (saturated solution) substantially throughout the 24 hour delivery period. The initial NG loading would normally be in excess of the minimum loading. The maximum ethanol loading per $cm^2$ is determined by the ethanol flux required in the initial high delivery rate phase, the duration of the phase and the solubility of ethanol in its carrier. Because of the high permeability of skin to ethanol the desired fluxes can be obtained from sub-saturated sources having an activity less than 1. Ethanol fluxes within the selected ranges can be obtained if the initial loading of ethanol is sufficient to maintain the thermodynamic activity of ethanol above about 0.2 during the initial phase and thereafter drop below about 0.2 at $t_2$, the time of commencement of the low NG administration rate phase.

A typical NG-ethanol reservoir composition according to this invention comprises a dispersant having a low solubility, below about 5 mg/gm, for NG and ethanol and having the NG and the ethanol dispersed therethrough. To facilitate dispersion the NG and ethanol would be absorbed on a suitable carrier such as lactose for NG and porous polypropylene or colloidal silicon dioxide for the ethanol, for example, as disclosed in copending U.S. patent application of Gale et al., Ser. No. 730,714 filed May 3, 1985 for Transdermal Delivery System for Delivering Nitroglycerin at High Transdermal Fluxes.

The aforementioned patents and applications and U.S. Pat. No. 4,144,317, which is incorporated herein by reference, disclose various materials that can be used to form the backing, reservoir, rate controlling membrane and adhesive layers. A preferred NG delivery device according to this invention employs silicone medical fluid gelled with silica as the reservoir, colloidal silica or porous polypropylene as the ethanol absorbent and an EVA membrane having a minimum of 11% VA and preferably about 12–18% VA as the rate controlling membrane at a typical thickness of about 1–3 mils. The higher the VA content of the EVA, the greater the permeability to both NG and ethanol. The ethanol may be included as absolute alcohol although it is preferred, particularly from a cost standpoint to utilize the substantially less expensive aqueous USP 95% ethanol. More dilute ethanol solutions can be employed provided the ethanol activity is maintained above about 0.2 throughout the initial high delivery rate period and below 0.2 for the remainder of the useful life of the system.

Having thus generally described representative delivery devices according to the invention the following specific examples are provided.

EXAMPLE 1

A NG/ethanol reservoir composition comprising a silicone medical fluid carrier gelled with silica, having NG on lactose uniformly dispersed therethrough and ethanol absorbed in a particulate carrier is fabricated by placing 5 kg of silicone medical fluid having a viscosity of about 100 centistokes and 175 grams of colloidal silicon dioxide in a high energy mixing vessel and blending to produce a gelled silicone fluid. 200 grams of Accurel® porous polypropylene available from ARMAK Company is placed in a separate vessel and approximately 1100 grams of USP ethanol (95% ethanol) is added with stirring to produce an essentially dry, flowable powder which on visual observation appears to have absorbed substantially all of the ethanol. Five kg of nitroglycerin-lactose (10% wt nitroglycerin) and the ethanol loaded porous polypropylene are placed in the original high energy mixing vessel and mixed until a homogeneous blend is obtained. A pouching machine is used to pouch the NG-ethanol gel so formed between an impermeable backing member comprising a medium density polyethylene/aluminized polyester/ethylene vinyl acetate multilaminate (Medpar® 1006 available from Minnesota Mining Manufacture Company) peripherally thermosealed to the rate controlling membrane layer of a trilaminate film consisting of a release liner layer formed from polyester film coated with a film release agent, an adhesive layer formed of silicone medical adhesive and release rate controlling membrane layer formed from a 1.5 mil thick EVA (12% VA) membrane to produce NG and ethanol loadings of 2.6 mg/cm² and 4.8 mg/cm² respectively. Systems can be fabricated having NG/ethanol releasing surface areas of varying sizes such as approximately 5 cm², 10 cm² and 20 cm², for example. In vivo blood concentrations to be obtained upon the application of a 5 cm² system to a normal human subject compared to those obtained from a similarly sized commercially available Transderm-Nitro delivery devices shown in FIG. 8.

EXAMPLE 2

A transdermal therapeutic device was fabricated according to procedure of Example 1 except thtt the ethanol is absorbed on 200 grams of colloidal silicon dioxide. The performance will be substantially the same as for the device of Example 1.

EXAMPLE 3

A device similar to that of Example 1 was fabricated using EVA (18% VA) film instead of the EVA (12% VA) film and with loadings of 5 mg NG/cm² and 20 mg ethanol/cm². The device will perform in a manner similar to that of Example 1 except the initial high steady state delivery rate will be about 80% thereafter.

Having thus generally described out invention and preferred specific embodiments thereof it is apparent that various modifications and substitutions can be made by workers skilled in the art without departing from the scope of this invention which is limited only by the following claims wherein:

We claim:

1. A medical device for the pulsitile administration of a drug through intact skin at a first steady state flux during a first delivery period and a second steady state flux during a second delivery period, said first and second delivery periods comprising a substantial portion of a predetermined administration period; said device comprising:
   (a) a reservoir of said drug containing an amount of drug at least sufficient to administer drug at said first and second steady state fluxes throughout said administration period, said first steady state flux being substantially higher than said second steady states flux
   (b) a reservoir of a skin permeation enhancer for said drug; said reservoir containing an amount of permeation enhancer (i) sufficient to permit administration of said permeation enhancer at permeation enhancing fluxes through said first delivery period and (ii) insufficient to permit administration of said permeation enhancer at permeation enhancing fluxes during the remainder of said administration period; and
   (c) means for maintaining said device on the skin in drug and permeation enhancer transferring relationship thereto; whereby a pulsitile drug administration pattern, having a first flux substantially higher than the flux of drug through untreated skin during said first period and a second, substantially lower flux during said second delivery period, will be obtained.

2. The device of claim 1 wherein said drug reservoir and permeation enhancer reservoir is a common reservoir comprising drug and permeation enhancer dispersed within a carrier.

3. The device of claim 1 further comprising release rate controlling means for one of said drug and permeation enhancer disposed between the respective reservoir and the skin.

4. The device of claim 3 wherein said release rate controlling means controls the release rate of said permeation enhancer and is disposed between the permeation enhancer reservoir and the drug reservoir and in the flow path of permeation enhancer from said enhancer reservoir to the skin.

5. The device of claim 4 wherein said drug reservoir comprises the skin contacting surface of the device.

6. The device of claim 5 wherein said drug reservoir comprises said drug dispersed within an adhesive and said drug reservoir comprises the means for maintaining the device on the skin.

7. The device of claim 2 further comprising release rate controlling means for one of said drug and permeation enhancer disposed between the common reservoir and the skin.

8. The device of claim 7 wherein said means for maintaining the device on the skin comprises a contact adhesive on the skin contacting surface of the device.

9. The device of claim 3 wherein said release rate controlling means controls the release rate of said drug during said first delivery period and is disposed between said drug reservoir and said enhancer reservoir in the path of drug flow from said drug reservoir to the skin.

10. The device of claim 7 wherein said release rate controlling means controls the rate of release of said permeation enhancer.

11. The device of claim 7 wherein said release rate controlling means controls the release rate of said drug during said first delivery period.

12. The device of claim 1 wherein said drug is permeable through normal human skin at therapeutic fluxes.

13. The device of claim 12 wherein said drug is selected from the group consisting of analgesics, antiemetics, anti-inflammatories, anti-anginals and anti-spasmodics.

14. The device of claim 1 wherein said drug is nitroglycerin and said permeation enhancer is ethanol.

15. A medical device for the pulsatile administration of nitroglycerine through intact skin at a first steady state flux during a first delivery period, and a second steady state flux during a second delivery period, said first flux being higher than said second flux, said first and second delivery periods comprising a substantial portion of a predetermined administration period, said device comprising:
   (a) a nitroglycerin reservoir;
   (b) an ethanol reservoir; and
   (c) means for controlling the release rate of said ethanol;
      said device being characterized by having a $J_{device}$ for nitroglycerin of at least about 28 µg/cm²/hr, a $J_{device}$ for ethanol in the range of 300–750 µg/cm²/hr, said ethanol reservoir containing that amount of ethanol required to allow the activity of the ethanol in the reservoir to drop below about 0.2 at the end of said first delivery period and said nitroglycerin reservoir containing sufficient nitroglycerin to supply nitroglycerin at said first and second steady state fluxes at least until the expiration of said predetermined administration period.

16. The device of claim 15 wherein said first delivery period is at least 2 hours, said second delivery period is at least 2 hours, and said predetermined administration period is at least about 16 hours.

17. The delivery device of claim 16 wherein each of said first and second delivery periods is at least 6 hours.

18. The delivery device of claim 17 wherein said administration period is at least about 24 hours.

19. The delivery device of claim 1 where each of said first and second delivery periods is at least 2 hours and said administration period is at least about 16 hours.

20. The delivery device of claim 19 wherein each of said first and second delivery periods is at least 6 hours.

21. The delivery device of claim 20 wherein said administration period is at least about 24 hours.

22. The device of claim 15 wherein said nitroglycerin reservoir and said ethanol reservoir comprises a common reservoir of nitroglycerin and ethanol in a carrier having solubility for nitroglycerin and ethanol of no more than about 5 µg/gm.

23. The device of claim 15 wherein said rate controlling means is formed from ethylene vinyl acetate copolymer having a vinyl acetate content from about 11-18%.

24. The device of claim 22 wherein said rate controlling means is formed from ethylene vinyl acetate copolymer having a vinyl acetate content of from about 11-18%.

25. A method for pulsatile transdermal drug delivery from a medical device applied to the skin during an administration period which comprises:
(a) coadministering a drug and a permeation enhancer for the drug from said medical device during a first delivery period; and
(b) thereafter administering said drug and no more than an enhancement ineffective amount of said permeation enhancer from said device for a second delivery period, said first and second period each being at least about 2 hours, said first and second periods comprising a substantial portion of said administration period.

26. The method of claim 25 wherein said administration period is at least about 16 hours.

27. The method of claim 25 wherein said first and second periods are each at least about 6 hours and said administration period is at least about 24 hours.

28. The method of claim 25 wherein said drug is nitroglycerin, said enhancer is ethanol, the activity of said ethanol in the device is above about 0.2 during said first period and below about 0.2 during said second period.

29. The method of claim 28 wherein the activity of said nitroglycerin in the device is maintained at unit activity substantially throughout said administration period.

30. A method for pulsatile transdermal delivery of a drug in which comprise maintaining a source of drug in drug transmitting relationship to the skin and delivering said drug through skin from said source at a first rate substantially higher than the maximum rate at which said drug permeates through untreated intact skin and thereafter administering said drug at a second rate no greater than the rate at which said drug permeates through untreated skin.

31. The method of claim 30 wherein said first and second periods are at least 2 hours.

32. The method of claim 31 wherein said first and second periods are at least 6 hours.

33. The method of claim 30 wherein said drug is nitroglycerin.

34. The method of claim 31 wherein said drug is nitroglycerin.

35. The method of claim 32 wherein said drug is nitroglycerin.

* * * * *